United States Patent [19]

LaDuca

[11] Patent Number: 5,318,910
[45] Date of Patent: Jun. 7, 1994

[54] STANDARD WHOLE BLOOD COMPOSITION FOR DETERMINING THE POTENCY OF BLOOD CLOTTING INHIBITORY SUBSTANCES

[75] Inventor: Frank M. LaDuca, East Brunswick, N.J.

[73] Assignee: International Technidyne Corp., Edison, N.J.

[21] Appl. No.: 4,495

[22] Filed: Jan. 14, 1993

Related U.S. Application Data

[63] Continuation of Ser. No. 809,859, Dec. 18, 1991, abandoned, which is a continuation of Ser. No. 269,469, Nov. 10, 1988, abandoned.

[51] Int. Cl.$^5$ ............................................. G01N 31/00
[52] U.S. Cl. ........................................ 436/8; 430/11; 430/16; 430/63; 430/69
[58] Field of Search .................... 436/8, 9, 10, 11, 12, 436/13, 14, 15, 16, 17, 18, 63, 69; 252/408.1

[56] References Cited

U.S. PATENT DOCUMENTS

| | | | |
|---|---|---|---|
| 4,250,041 | 2/1981 | Babson et al. | 436/17 |
| 4,489,162 | 12/1984 | Hankins et al. | 436/17 |
| 4,731,330 | 3/1988 | Hill et al. | 436/69 |
| 4,871,677 | 9/1989 | Baugh et al. | 436/18 |

*Primary Examiner*—James C. Housel
*Assistant Examiner*—Lien Tran
*Attorney, Agent, or Firm*—Plevy & Associates

[57] ABSTRACT

A standard whole blood composition is disclosed, which is useful as a pooled human hemostasis reference standard in blood coagulation assays including Activated Clotting Time (ACT), Whole Blood Prothrombin Time (WBPT), Whole Blood Activated Partial Thromboplastin Time (WBAPTT) and Whole Blood Thrombin time (WBTT). Also disclosed are methods for determining the human standardized potency of heparin and protamine.

31 Claims, No Drawings

STANDARD WHOLE BLOOD COMPOSITION FOR DETERMINING THE POTENCY OF BLOOD CLOTTING INHIBITORY SUBSTANCES

This is a continuation of application Ser. No. 07/809,859, filed on Dec. 18, 1991 abandoned, which is a continuation of application Ser. No. 07/269,469 filed on Nov. 10, 1988 abandoned.

BACKGROUND OF THE INVENTION

This invention relates to a standard whole blood composition, methods for making the composition and methods for determining the potency of blood clotting inhibitory substances.

Fundamental to human life and well being is the ability of human blood, in response to certain stimuli, to thicken and eventually form structures known as blood clots. Blood clotting occurs in response to both external and internal bleeding. Conversely, unwanted clot formation or blood thickening can have undesirable effects among which are circulatory blockages. Certain medical procedures, for example cardiopulmonary bypass (CPB), are obviously adversely affected by blood clotting and would not be possible without means to prevent blood clot formation.

Medical science has developed pharmacological agents which modify the inherent clotting characteristics of human blood. These substances are widely used to treat diseases and to perform medical procedures. A substance of major importance is a naturally occurring material known as heparin. Heparin is a polysaccharide sulfuric acid ester found especially in lung, liver and intestinal tissue and has the ability in certain circumstances to prolong the clotting time of blood. Commercially available heparin is derived from animal tissues principally porcine intestine or bovine lung. As presently understood, commercially processed heparin is a complex substance and its pharmacological activity per unit weight may vary depending on the characteristics of a specific batch of material.

Heparin is sold with its biological potency expressed in U.S.P. units. U.S.P. units are related to the clot formation inhibition of heparin mixed with sheep plasma (blood with all cells removed by centrifugation), *The United States Pharmacopeia*, 21st Edition (1985) pp. 481–482.

It is well known that there are significant differences in the body's clotting systems (i.e., the blood solids including red blood cells, white blood cells and platelets and the circulatory coagulation factor proteins associated with the plasma) among different individuals. While healthy persons may exhibit blood clotting within so called normal ranges, the actual physiological performance of their system may exhibit wide variations. The production and metabolism of the classical coagulation factors, for example, can vary within fairly wide ranges. One can readily see therefore that care must be used in predicting the response of a given individual to medications affecting coagulation or in developing data based on a blood sample from one donor which can be expected to be applicable to the general population.

Whole blood clotting and plasma clotting involve different mechanisms and substances. Plasma lacks many elements present in whole blood, namely platelets, red blood cells, and white blood cells, which are intricately involved in the hemostatic process. Since heparin is known to interact with these elements, it is readily apparent that the failure of traditional laboratory assays that are typically based on analysis of blood plasma, e.g., the prothrombin time (PT) or the Activated Partial Thromboplastin Time (APTT) test, to monitor heparin anticoagulation effect is due to the inability to duplicate in the lab the true hemostatic status of the patient. Moreover, human blood plasma and sheep blood plasma (used in the U.S.P. assay) are obviously different in their clotting response. Because of these factors, the blood clotting inhibition response of a particular human to a dose of heparin from a particular manufacturer's batch of heparin is somewhat unpredictable.

Medical science has developed various techniques to measure the clotting ability of a sample of human blood. A commonly used procedure is the determination of the blood's Activated Clotting Time (ACT). See, for example, Hattersley, P., *JAMA*, 196:150–154, 1966; LaDuca F., et al., *J. Extra-Corpor. Technol.*, 19:358–364, 1987; and Dutton et al., *Anaesthia*, 38:264–68, 1983. In this method the amount of time required for a 0.5 to 2.0 ml sample of the patient's blood to clot is measured. A normal ACT range is 140 to 180 seconds for a population of patients with cardiovascular disease. The ACT range for the general population is 120 to 140 seconds.

During a CPB procedure heparin will typically be administered to the patient to inhibit clot formation so as to achieve ACT values of greater than 480 seconds. Bull, B., et al., *J. Thorac. Cardiovasc. Surg.*, 69:685–689, 1975. At the conclusion of the surgical procedure the heart lung machine is disconnected and there is no further need to inhibit blood clot formation. While the previously infused heparin would eventually leave the patient's body, one can see that it is medically imperative to restore the patient's blood clotting ability to prevent uncontrolled bleeding. The normal blood clotting state is called clinical hemostasis.

In order to achieve hemostasis, it is common to administer a substance known as protamine to the heparinzed patient. Protamines are simple strongly basic proteins of relatively low molecular weight. These proteins are water soluble, not coagulated by heat and yield only amino acids, chiefly arginine when hydrolyzed.

Protamine is a naturally occurring material and is commercially available to the medical profession as an extract from certain fish (salmon) tissue. The purity and therefore the physiological potency of commercial protamine preparations, for reasons not well understood, have been shown to vary from batch to batch. Protamine is dispensed on a weight basis. Protamine, while of different chemistry than heparin, also has the property of prolonging the blood clotting time in humans.

Heparin and protamine are reactive with each other on a stoichiometric basis. Heparin is an anionic substance and protamine is a cationic substance. When the two substances are mixed in blood (either in vivo or a test tube) they react quantitatively to form a neutral (and physiologically inactive) entity. Medical personnel therefore infuse protamine at the conclusion of, e.g., a CPB procedure, to neutralize heparin in patient's blood and restore normal, baseline blood clotting ability.

Protamine, however, as previously discussed, is itself an anticoagulant and if excess protamine is infused, hemostasis will not be achieved. Further complications can result from the fact that protamine may be toxic to some individuals—Horrow, J., *Anesth. Analg.*, 64:348-361, 1985. Protamine is also reportedly capable of inducing an allergic response in certain patients—Sharath, M., et al., *J. Thorac. Cardiovasc. Surg.*, 90:86-90, 1985.

Surgical teams performing thoracic surgery typically follow one of three procedures to estimate the dosage of protamine required to neutralize the heparin circulating in the patient's blood. One method is to administer protamine based on a ratio of protamine to total heparin infused during the procedure. As previously discussed, the physiological potency of heparin and of protamine vary from batch to batch and one can foresee the potential for inaccuracies.

Another method employs a procedure based on the heparin dose—response curve described by Bull, B., et al., *J. Thorac. Cardiovasc Surg.*, 69:685-689, 1975. At the end of cardiopulmonary bypass the concentration of heparin remaining in the patient's blood is determined by correlation of the ACT to a dose-response curve of ACT vs. heparin concentration constructed prior to bypass. Once the blood heparin concentration is known, an empirical protamine to heparin ratio is used to calculate a protamine dose which will neutralize the patient's heparin and restore clinical hemostasis.

At the present time the preferred clinical method is heparin vs. protamine titration in vitro wherein varying amounts of liquid protamine are added to heparinized blood to determine the amount of protamine required to normalize whole blood clotting times measured by the Activated Clotting Time (ACT) test. The clinical use of a protamine titration assay based on ACT technology has been limited due to the lack of a convenient and accurate protamine assay.

Irrespective of the availability of the ACT assay, it is not possible to predict how a given patient will respond to a given heparin or protamine preparation. This is primarily due to the fact that, as currently labeled, heparin or protamine preparations do not indicate the potency of the drug in a human characterized blood specimen. Currently the accepted pharmaceutical labeling of potency is the United States Pharmacopeia (USP) designation. As noted above, the USP designation of heparin potency is the anticoagulant inducing effect of heparin in a substrate of animal (sheep) citrated plasma. Conversely, protamine potency is the neutralization of heparin in this same substrate. This is referred to as the heparin neutralizing potency. There are two obvious deficiencies of this system. First the non-human substrate used does not behave the same as human material. Secondly, the substrate is citrated plasma and, for the aforementioned reasons, plasma has not proven an effective substitute for human blood as a tool to predict anticoagulant response. In sum, due to the complexity of the coagulation mechanism, the prior art methods and substances have very serious drawbacks.

SUMMARY OF THE INVENTION

I have now discovered a standard whole blood composition (SWB composition) that can alleviate or overcome the drawbacks discussed above. The composition comprises (a) platelet poor plasma from at least four human donors, (b) a sufficient amount of a calcium chelating agent to prevent clotting of the composition, and (c) blood solids comprising red blood cells and platelets from at least one human donor having a blood type which will not agglutinate with the platelet poor plasma.

The SWB composition represents the average clotting activity present in the average population. It thus more closely resembles whole blood in its clotting response than currently available substrates (e.g. human or sheep plasma) and allows a clinician or laboratorian the means to duplicate in the laboratory a material reflective of a patient's actual clotting ability, because it contains all the essential, interactive components, i.e., plasma factors, platelets, red blood cells and in general white blood cells.

The SWB composition can be used to standardize the potency of heparin relative to human blood, rather than the sheep plasma. As noted above, how heparin affects sheep plasma many times is not indicative of how it will react in human blood. The present composition will thus help alleviate these variations in response by providing a material for assaying heparin which better simulates the environment in which the heparin is actually employed.

Moreover, because of its characteristics, the SWB composition is useful in standardizing the potency of unknown heparin and protamine samples, in determining the anticoagulation effect of heparin in patient blood samples and in determining the neutralizing effect of a particular protamine sample. Heparin can thus be standardized in terms of "human characterized anticoagulant units" and protamine in terms of "human characterized neutralization potency." Also, an individual's response to heparin or protamine is compared to a known standard, i.e., the SWB composition of the invention, will provide clinicians with an indication of how a particular patient's response will vary from the normal response.

One aspect of the invention involves a method for determining the anticoagulant effect of a heparin sample comprising (a) mixing a predetermined amount of heparin with the SWB composition, the heparin being present in a clinically effective concentration in the composition, (b) adding calcium ions in a predetermined amount to the heparin/SWB composition mixture sufficient to provide free (non-chelated) calcium in such mixture and allow the mixture to form a clot, and (c) measuring the clotting inhibition caused by the heparin sample. Preferably, the measuring step is performed by (a) contacting the heparin/SWB/calcium ion composition mixture with a coagulation contact activation agent, and (b) measuring the time from such contacting to the first detectable clot formation. By comparing such time to the time needed to clot an actual patient's blood subject to the same amount of heparin, a measure of patient's blood clotting ability can be obtained.

Another aspect of the invention comprises (a) mixing a predetermined amount of a protamine sample with the SWB composition containing heparin in a predetermined concentration in the composition, (b) adding calcium ions in a predetermined amount to the protamine sample/heparin/SWB composition mixture sufficient to provide free (non-chelated) calcium in such mixture and allow the mixture to form a clot, and (c) measuring the neutralizing effect of such protamine sample on the heparin in clotting the SWB composition. The measuring step is preferably performed by (a) contacting the protamine sample/heparin/SWB composition mixture with a coagulation contact activation agent, and (b) measuring the time from such contacting to the first detectable clot formation, e.g., in the ACT assay.

DETAILED DESCRIPTION OF THE INVENTION

The platelet poor plasma is collected from at least four human donors in a conventional manner. For example, whole blood can be collected from a donor by atraumatic venipuncture using a two syringe technique with a butterfly needle. The needle may be removed from the syringe and the blood collected in a citrate containing tube, e.g., a centrifuge tube. The tube may be sealed and mixed (not shaken). Usually, the tube is placed in an ice bath and centrifuged at about 1600–2400×g, preferably about 1800–2200×g, for about 15 to 25 minutes, more preferably about 2000×g for about 20 minutes or more, at about 4° C. The platelet poor plasma can be collected with a plastic pipette, being careful not to remove the buffy coat at the interface of the red blood cells and plasma. The plasma may then be pooled with the plasma from other donors, mixed thoroughly and frozen in an ultra-low freezer, e.g., at less than about −30° C., or the individual plasma sample can be stored first and mixed (pooled) later. The plasma can be thawed by placing in a water bath at a suitable temperature, e.g., about 37° C., prior to use in the present invention. Freshly collected plasma may also be employed.

Platelet poor plasma is a term well known in the art. It generally refers to plasma containing few, if any, platelets and essentially no red or white blood cells. Preferably, the platelet poor plasma contains less than 10,000 platelets per μl, more preferably less than 2000 platelets per μl, but plasma essentially free of platelets may also be employed.

The blood solids are also collected by conventional techniques. For example, the buffy coat and red blood cell layers from the above described procedure for collecting platelet poor plasma may be employed. The collected blood solids may be pooled with blood solids from other blood compatible donors, if desired, then stored, if necessary, for several days at low temperature, e.g. from about 2°–8° C., or the blood solids may be stored individually and later pooled, with blood solids from other compatible donors, if desired.

The SWB composition of the invention preferably contains more than about 200,000 platelets per μl, more preferably greater than about 400,000. Typically, the SWB composition contains from about 200,000 to about 600,000 platelets per μl. The SWB composition also preferably contains from about $2.5 \times 10^6$ to about $6.5 \times 10^6$, more preferably from about $4 \times 10^6$ to about $5 \times 10^6$, red blood cells per μl and contains from about $2 \times 10^3$ to about $10 \times 10^3$, more preferably $3 \times 10^3$ to $7 \times 10^3$ white blood cells per μl.

The blood solids preferably contain platelets, red blood cells and white blood cells. However, if desired, the white blood cells may be omitted. Removal of the white blood cells may be accomplished by techniques well known in the art.

The SWB composition contains a calcium chelating agent. By chelating the calcium in the SWB composition, clotting of the composition is prevented. The clotting mechanism can be reinitiated by adding calcium ions to the composition in an amount sufficient to have free (non-chelated) calcium in the composition. Preferably, the calcium is added in an amount so as to exceed the average or normal calcium concentration in human blood. The calcium chelating agent is present in the SWB composition in concentrations of from about 0.012 to about 0.018 Molar. More preferably, the calcium chelating agent is present in the composition in a concentration of from about 0.014 to about 0.016 Molar.

Any suitable calcium chelating agent which has no known interaction with the blood coagulation factors may be employed. A preferred calcium chelating agent is a citrate salt, e.g., sodium citrate, potassium citrate, acid citrate dextrose (ACD), citrate phosphate dextrose (CPD), etc. More preferably, the calcium chelating agent is sodium citrate.

Typically, the whole blood for the collection of platelet poor plasma and blood solids for the SWB composition are collected directly into a citrated plastic tube. For example, about 9 ml of donor blood is collected into about 1 ml of approximately 3.8% by weight sodium citrate solution.

In one embodiment, the blood solids are from at least one human donor having type O blood. When the blood solids are from a type O donor, the platelet poor plasma may be from donors having any blood types, i.e., O, A, B, or AB. However, if the blood solids are from at least one donor having type A, B or AB type blood, the platelet poor plasma is from donors having the same type blood as the blood solids donors, i.e., to prevent agglutination.

The ratio of blood solids to platelet poor plasma in the SWB composition is preferably from about 1:1 to about 1:4 by volume and more preferably from about 1:1.5 to about 1:3.5 by volume. Usually, a ratio of blood solids to platelet poor plasma of about 1:2 by volume is employed.

By employing more donors for the platelet poor plasma and for the blood solids, an SWB composition more representative of the blood clotting ability of the mean normal human population can be obtained. Thus, the variability of single individuals, be they above or below normal in clottability, are blended to make a preparation indicative of the clottability of an average individual. In a preferred embodiment the platelet poor plasma is obtained from at least about 10 human donors, more preferably from at least about 20 human donors. The blood solids are preferably obtained from at least about 4 human donors and more preferably from at least about 10 human donors. Donors for the platelet poor plasma and for the blood solids may be the same, but preferably at least some of the donors for each component are different.

The donors for the platelet poor plasma and for the blood solids should be healthy, unmedicated individuals. They should be donors having all the factors necessary for normal blood clotting, i.e., they should not be hemophiliacs lacking one or more clotting factors. They should also be individuals who have not taken any medication which affects the clottability of blood, e.g., they should not have taken aspirin or antihistamines.

The blood solids are preferably obtained from donors having a negative Rh factor. If the blood solids are obtained from donors having a positive Rh factor, the platelet poor plasma is also preferably from Rh positive donors.

The SWB composition can be prepared by mixing the pooled platelet poor plasma, the calcium chelating agent and the blood solids, as described above. Normally, the calcium chelating agent is already part of the pooled plasma and blood solids, as is conventional in the art, and the citrated blood solids and plasma may then be mixed to form the SWB composition.

The SWB composition may be stored at low temperature, preferably between about 2° and about 8° C. The SWB composition has been found to be stable at room temperature for four hours and maybe more.

The SWB composition can be used to determine the anticoagulant effect of a heparin sample or to determine the heparin neutralizing potency of a protamine sample. In the former method, a predetermined amount of a heparin sample is mixed with the SWB composition, with the heparin being present in a clinically effective concentration in the composition. Suitable concentrations of heparin are in the range of from about 1 to about 5 U.S.P. units of heparin per ml of blood compositions. The composition is recalcified with a sufficient amount of calcium ions to provide non-chelated calcium and allow the composition to clot. Typically, calcium ions are added so as to achieve a concentration from about 0.007 to about 0.009 Molar, preferably about 0.0079 to about 0.0081 Molar.

The clottability of a blood sample or the inhibition caused by heparin or protamine can be measured by any suitable technique. Among the various methods that may be employed include the activated clotting time (ACT) assay, prothrombin time (PT) assay, activated partial thromboplastin time (APTT) assay and thrombin time (TT) assay. See, for example, Hougie, C., *Hematology*, Edited by Williams, W., McGraw Hill, 3rd Ed., 1983, pp. 1662-1668. Preferably, the measuring is performed by contacting the heparin/SWB composition mixture with a coagulation contact activation agent and then measuring the time from such contacting to the first detectable clot formation.

In the preferred embodiment, the heparin determination is performed by the ACT assay. In this method, the blood substrate (in the presence of calcium) is mixed with a particulate coagulation activator, e.g., diatomaceous earth, celite or silica, and the length of time to detectable clot formation is determined while maintaining the sample at about 37° C. Hattersley, P., *JAMA*, 196:150-154, 1966.

The method for determining the heparin neutralizing potency of a protamine sample is performed similarly to the methods described above, except that a predetermined amount of protamine is mixed with the SWB composition containing a standard heparin (e.g., USP heparin of a particular potency) in a predetermined concentration. The neutralizing effect of the protamine sample on the heparin in clotting the SWB composition is then measured, e.g., by adding calcium ions in a predetermined amount to the protamine sample/heparin/SWB composition mixture sufficient to provide free (non-chelated calcium) in such mixture and allow the mixture to form a clot, contacting the protamine/heparin/SWB composition mixture with a suitable coagulation contact activation agent and then measuring the time from such contacting to the first detectable clot formation.

The SWB composition is thus very useful in determining the relative potency of heparin or protamine samples relative to standard heparin or standard protamine materials of known activity. The clot time for a heparin or protamine sample is determined in the method of the invention (e.g., the ACT test) and compared to the clot time for a heparin or protamine sample of known activity in the same method. Such standardization of protamine potency is also useful in determining how much of a particular protamine sample will be necessary to neutralize the heparin in a patient's blood, e.g., a patient having just completed a CPB procedure.

In the above methods, any suitable coagulation contact activation agent may be employed which will initiate the clotting of the SWB composition, e.g., a diatomaceous earth, celite or silica in the ACT assay or thromboplastin-like activity in the PT assay. A preferred coagulation contact activation agent is diatomaceous earth. Also, as is conventional in the art for such methods, the temperature should be fixed or constant, usually between about 36° to about 38° C., preferably about 37° C. Further, the mixing, adding, contacting and measuring the time from the contacting to the first detectable clot formation may be repeated at varying heparin sample and protamine sample concentrations to obtain a titration analysis of heparin sample concentration vs. clotting time or protamine sample concentration vs. clotting time to a first detectable clot, i.e., a dose-response plot.

The detection of clot formation can be accomplished by any suitable means conventional in the art for such purpose, e.g., by visual examination for a clot or by a mechanical or optical detection device. In a preferred embodiment, clot formation is detected by a Hemochron ® model 400 or 800 system for in vitro determination of blood coagulation time. See also U.S. Pat. Nos. 3,695,842 and 3,836,333. The HEMOCHRON ® clot detection mechanism consists of a magnetic detector positioned just below the inclined test tube containing the sample to be assayed. A cylindrical bar magnet within the tube remains in close proximity to this detector as the tube is slowly rotated about its axis of symmetry. When a fibrin mass forms, its adhesion to the magnet and to a plastic structure wedged into the tube causes the magnet to rotate with the tube. The magnet is thereby displaced from its initial position adjacent to the detector. A seconds timer, electrically connected to the magnetic detector, displays the time interval between test initiation and the end point (as determined by displacement of the magnet).

The following examples are intended to illustrate, but not to limit, the present invention.

EXAMPLE 1

Blood is collected into plastic containers by fresh venipuncture from four healthy, unmedicated donors having blood type O negative. Each blood sample is collected into one-tenth volume of 3.8% sodium citrate so as to prevent clotting of the sample. Each blood sample, after being thoroughly mixed with the citrate at room temperature, is placed into a laboratory centrifuge and centrifuged at 2,000×g for 20 minutes. When centrifugation is completed, the supernatant plasma is withdrawn from the sample using a plastic pipet. The buffy coat at the interface of the red blood cells (RBC) and plasma is not removed. The blood solids (i.e. red blood cells, white blood cells and platelets) from these donors are pooled in a suitable plastic container and mixed.

Normal Pooled Plasma (NPP) is prepared by collection of citrated blood from ten healthy, unmedicated donors in a manner similar to that described above. The blood samples are collected without regard to blood type (A, B, O, AB). Each blood sample is centrifuged as described above and the supernatant plasma withdrawn, pooled and frozen at about −30° C.

To prepare the SWB composition, a sample of the NPP is removed from the freezer and thawed in a 37° C. water bath. With all materials at room temperature, 1 part by volume of the pooled blood solids mixture is added to 2 parts by volume of the thawed NPP. This preparation is mixed on a shaker for 15 minutes prior to use.

EXAMPLE 2 QUANTIFICATION OF PROTAMINE POTENCY

Protamine characterization is the quantification of the heparin neutralizing potency of a given protamine preparation compared to a reference protamine preparation. The SWB composition described in Example 1 above is heparinized using a USP referenced heparin preparation. A standard amount of reference protamine and a protamine of unknown potency are added to samples of the heparinized preparations for the purpose of performing a titration assay. Heparin neutralization is monitored by the ACT assay. A titration curve of ACT versus protamine concentration is prepared for each protamine sample. By extrapolation of the titration curve to the baseline ACT value (e.g., the ACT value of the SWB composition lacking heparin and/or protamine), the amount of protamine required to completely neutralize the heparin in the blood sample is calculated. A comparison of the protamine required for neutralization of the reference and the unknown protamine is a measure of the relative potency of the protamine preparation. This proportion is referred to as the protamine Index Factor.

PREPARATION OF MATERIALS

PROTAMINE: The protamine of unknown potency is diluted to a final concentration of 1 mg/ml in 0.9% sodium chloride.

REFERENCE PROTAMINE: The reference protamine is prepared in a similar manner to yield a preparation of 1 mg/ml. The reference protamine is standardized as to potency against the master lot of material, the master lot having been originally quantified, using a USP assay, as having a heparin neutralizing potency of approximately 118 units of USP heparin per mg of protamine.

REFERENCE HEPARIN: A USP referenced heparin preparation is diluted in 0.9% sodium chloride to yield a final concentration of 100 units/mi.

CALCIUM CHLORIDE: Calcium chloride is dissolve in distilled, deionized water to a final concentration of 0.025 Molar.

CLOT DETECTION DEVICE: A Hemochron® model 800 system is employed.

PROCEDURE Materials

Standard Whole Blood composition of Example 1
Reference protamine (1 mg/ml)
Test protamine (to be Indexed, 1 mg/ml)
Reference USP heparin (100 units/ml)
calcium chloride (0.025M)
plastic 12×75 test tubes
HEMOCHRON® Coagulation timers
HEMOCHRON®ACT test tubes containing about 12mg of celite saline (0.9% NaCl)

1. Add 24 microliters of the reference and test protamine to each of two plastic test tubes.
2. Heparinize a sample of the SWB composition to a final heparin concentration of 2.0 units per ml by adding 20 microliters of the USP heparin per each one ml of SWB.
3. Add 1.6 ml of heparinized SWB to one of the test tubes prepared in step number 1.
4. Vortex for 3-5 secs.
5. Add 0.8 ml calcium chloride to the same tube.
6. Vortex for 3-5 secs.
7. Transfer 2.0 ml of the mixture to a Hemochron® ACT test tube.
8. Start the Hemochron® timer.
9. Agitate the tube 5 times vigorously.
10. Place in the tube in the Hemochron® test well.
11. Record the ACT.
12. Repeat steps 3 through 11 for each test tube prepared in step 1.

Control Preparations

1. Add 24 microliters of saline to four plastic test tubes.
2. To two tubes add SWB (unheparinized) and perform steps 3 through 11 above.
3. To two tubes add SWB (heparinized) and perform steps 3 through 11 above.

Results

1. Record the ACT values for the duplicate samples tested above. Determine the mean value for each sample.
2. Prepare a sheet of standard graph paper displaying the ACT values on the y axis (range 0-1000 secs) and the protamine concentration on the X axis (range 0-60 micrograms/ml).
3. Plot the ACT value of the unheparinized SWB on the graph. Draw a horizontal line at this ACT value. This is the baseline ACT.
4. Plot the ACT value of the heparinized SWB on the graph. This is the Status-ACT.
5. At a protamine concentration of 15 micrograms/ml plot the mean ACT values of the samples tested containing the reference protamine.
6. Draw a straight line from the status ACT value through this protamine ACT value and extending to the intercept of the baseline ACT value.
7. At a protamine concentration of 15 micrograms/ml plot the mean ACT values of the samples tested containing the test protamine (as per step 5).
8. Draw a straight line through the status ACT and this value as in step 6.
9. Read down vertically to the X-axis to determine the protamine concentration at the intercept of each titration line with the baseline ACT. This value is the Unit Protamine Concentration (UPC)

Interpretation

The protamine index factor is determine by the following formula:

$$\frac{UPC \text{ test}}{UPC \text{ reference}} = \text{Index Factor}$$

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What is claimed is:

1. A method of quantifying the potency of heparin, comprising the sequential steps of:
   pooling plasma derived from blood of at least four human donors;

collecting blood formed elements including unfixed viable red blood cells and platelets from at least one human donor having a blood type that does not agglutinate with said plasma;

combining said plasma and said blood formed elements to form a whole blood composition;

adding a calcium chelating agent to said whole blood composition in an amount that prevents clotting within the composition;

mixing a predetermined amount of heparin with said whole blood composition to form a heparin blood composition mixture;

adding calcium ions to said heparin blood composition mixture in an amount that enables the mixture to clot; and measuring the time it takes for said heparin blood composition mixture to clot, where the time measured is a function of the potency of said predetermined amount of heparin added;

determining the potency of said predetermined amount of heparin from said measured time.

2. The method according to claim 1, wherein said step of measuring includes:

contacting said heparin blood composition mixture with a coagulation contact activating agent, and measuring the time from such contact to the appearance of a detectable clot formation.

3. The method according to claim 1, wherein said plasma contains less than 10,000 platelets per $\mu l$.

4. The method according to claim 1, wherein said step of collecting blood formed elements includes collecting blood formed elements from a plurality of human donors.

5. The method according to claim 1, wherein said blood formed elements further include white blood cells.

6. The method according to claim 1, wherein said blood formed elements are collected from type O blood.

7. The method according to claim 1, wherein said blood formed elements and said plasma are collected from donors of the same blood type.

8. The method according to claim 1, wherein said step of combining produces said whole blood composition having more than 200,000 platelets per $\mu l$, between $2.5 \times 10^6$ and $6.5 \times 10^6$ red cells per $\mu l$ and between $3 \times 10^3$ and $7 \times 10^3$ white blood cells per $\mu l$.

9. The method according to claim 1, wherein said step of adding a calcium chelating agent includes providing said calcium chelating agent in a concentration that is greater than a normal concentration of calcium found in human blood.

10. The method according to claim 1, wherein said step of adding calcium chelating agent includes providing said calcium chelating agent in concentration from 0.012 Molar to 0.018 Molar.

11. The method according to claim 1, wherein said calcium chelating agent is a citrate salt.

12. The method according to claim 1, wherein said step of combining includes combining blood formed elements to said plasma in a ratio of between 1:1 to 1:4 by volume.

13. The method according to claim 1, wherein said plasma is derived from the blood of at least 10 human donors and said blood formed elements are derived from at least 10 human donors.

14. The method according to claim 1, wherein said plasma and said blood formed elements are derived from the blood of different groups of donors.

15. The method according to claim 1, wherein said plasma and said blood formed elements are collected from donors having the same Rh factor.

16. A method of quantifying the potency of protamine, comprising the sequential steps of:

pooling plasma derived from blood of at least four human donors;

collecting blood formed elements including unfixed viable red blood cells and platelets from at least one human donor having a blood type that does not agglutinate with said plasma;

combining said plasma and said blood formed elements to form a whole blood composition;

adding a calcium chelating agent to said whole blood composition in an amount that prevents clotting within the composition;

mixing a predetermined amount of heparin with said whole blood composition to form first mixture;

mixing a predetermined amount of protamine with said first mixture to form a second mixture;

adding calcium ions to said second mixture in an amount that enables the second mixture to clot;

measuring the time it takes for said second mixture to clot, where the time is a function of a neutralizing effect of the protamine on said heparin thereby providing an indication of the potency of said predetermined amount of protamine;

determining the potency of said predetermined amount of protamine from said measured time.

17. The method according to claim 16, further including the step of comparing the time measured to a standardized time to produce an index factor indicative of the potency of said predetermined amount of protamine.

18. The methods according to claim 16, wherein said step of measuring includes:

contacting said second mixture with a coagulation contact activating agent; and measuring the time from such contact to the appearance of a detectable clot formation.

19. The method according to claim 16, wherein said plasma contains less than 10,000 platelets per $\mu l$.

20. The method according to claim 16, wherein said step of collecting blood formed elements includes collecting blood formed elements from a plurality of human donors.

21. The method according to claim 16, wherein said blood formed elements further include white blood cells.

22. The method according to claim 16, wherein said blood formed elements are collected from type O blood.

23. The method according to claim 16, wherein said blood formed elements and said plasma are collected from donors of the same blood type.

24. The method according to claim 16, wherein said step of combining produces said whole blood composition having more than 200,000 platelets per $\mu l$, between $2.5 \times 10^6$ and $6.5 \times 10^6$ red cells per $\mu l$ and between $3 \times 10^3$ and $7 \times 10^3$ white blood cells per $\mu l$.

25. The method according to claim 16, wherein said step of adding a calcium chelating agent includes providing said calcium chelating agent in a concentration that is greater than a normal concentration of calcium found in human blood.

26. The method according to claim 16, wherein said step of adding a calcium chelating agent includes providing said calcium chelating agent in concentration from 0.012 Molar to 0.018 Molar.

27. The method according to claim 16, wherein said calcium chelating agent is a citrate salt.

28. The method according to claim 16, wherein said step of combining includes combining said blood formed elements to said plasma in a ratio of between 1:1 to 1:4 by volume.

29. The method according to claim 16, wherein said plasma is derived from the blood of at least 10 human donors and said blood formed elements are derived from at least 10 human donors.

30. The method according to claim 16, wherein said plasma and said blood formed elements are derived from the blood of different groups of donors.

31. The method according to claim 16, wherein said plasma and said blood formed elements are collected from donors having the same Rh factor.

* * * * *